(12) United States Patent
Sugimoto et al.

(10) Patent No.: US 9,863,897 B2
(45) Date of Patent: Jan. 9, 2018

(54) X-RAY NONDESTRUCTIVE TESTING DEVICE

(71) Applicant: TOKYO ELECTRON LIMITED, Minato-ku, Tokyo (JP)

(72) Inventors: Naozo Sugimoto, Tokyo (JP); Toshihiko Nishizaki, Tokyo (JP); Masahiro Inoue, Tokyo (JP); Masuo Amma, Tokyo (JP); Masaru Nakamura, Tokyo (JP)

(73) Assignee: TOKYO ELECTRON LIMITED, Minato-Ku, Tokyo (JP)

( * ) Notice: Subject to any disclaimer, the term of this patent is extended or adjusted under 35 U.S.C. 154(b) by 343 days.

(21) Appl. No.: 14/844,168

(22) Filed: Sep. 3, 2015

(65) Prior Publication Data

US 2015/0377801 A1     Dec. 31, 2015

Related U.S. Application Data

(63) Continuation of application No. PCT/JP2013/055893, filed on Mar. 4, 2013.

(51) Int. Cl.
*G01N 23/083*     (2006.01)
*G01B 15/02*     (2006.01)

(52) U.S. Cl.
CPC .......... *G01N 23/083* (2013.01); *G01B 15/02* (2013.01)

(58) Field of Classification Search
None
See application file for complete search history.

(56) References Cited

U.S. PATENT DOCUMENTS 5,481,584 A * 1/1996 Tang ...................... G01N 23/06
                                                              378/53
5,841,833 A * 11/1998 Mazess ................... A61B 6/032
                                                              250/367

(Continued)

FOREIGN PATENT DOCUMENTS

JP     S53-003262         1/1978
JP     S58-062508 A       4/1983

(Continued)

OTHER PUBLICATIONS

International Search Report form PCT/ISA/210 for PCT/JP2013/055893 dated Jun. 18, 2013 (Jun. 18, 2013).

*Primary Examiner* — Hoon Song
(74) *Attorney, Agent, or Firm* — Nath, Goldberg & Meyer; Jerald L. Meyer

(57) ABSTRACT

There is provided an X-ray nondestructive testing device which irradiates X-rays to an article, the article including a substrate having a predetermined X-ray absorption coefficient and a measurement target object disposed therein and having another X-ray absorption coefficient differing from that of the substrate, the device including: an X-ray source configured to irradiate the X-rays to the article; a detector configured to detect the transmission amounts of the X-rays passed through the article at at least paired different locations; a detection position specifying designator configured to specify the paired different locations as a set of paired locations based on a pre-stored design information; a driving mechanism configured to move the detector to the set of paired locations; and an operation calculator configured to calculate the thickness of the measurement target object based on the transmission amounts of the X-rays detected by the detector.

14 Claims, 15 Drawing Sheets

(56) References Cited

U.S. PATENT DOCUMENTS

2013/0136230 A1* 5/2013 Arodzero ............. G01V 5/0016
    378/57
2013/0230139 A1* 9/2013 Morton ................ G01V 5/0066
    378/57

FOREIGN PATENT DOCUMENTS

| JP | S60-194304 A | 10/1985 |
| JP | H07-043320 A | 2/1995 |
| JP | H10-325714 A | 12/1998 |
| JP | 2000-249532 A | 9/2000 |
| JP | 2008-268076 A | 11/2008 |

* cited by examiner

X-RAY NONDESTRUCTIVE TESTING DEVICE

CROSS-REFERENCE TO RELATED APPLICATION

This application is a Continuation Application of PCT International Application No. PCT/JP2013/055893, filed Mar. 4, 2013, the entire contents of which are incorporated by reference herein.

TECHNICAL FIELD

The present disclosure relates to an X-ray nondestructive testing device which irradiates X-rays to a measurement target object residing inside an article such as a semiconductor, a printed substrate and the like, measures an amount of X-rays passed through the measurement target, and obtains a thickness of the measurement target object in a nondestructive manner without contacting the measurement target object.

BACKGROUND

As a method of measuring a thickness of an article having a predetermined X-ray absorption coefficient in a nondestructive manner, there is a method which includes irradiating X-rays to the article, measuring a transmission amount of X-rays passed through the article, and measuring a thickness of the article based on the transmission amount and the absorption coefficient.

In general, an article to be tested is provided with members made of various substances so that X-rays pass through the members along a path defined in the article. This makes it difficult to measure only a thickness of a member made of a certain substance inside the article.

In recent years, an article such as an electronic substrate, a wafer and the like, has a structure in which members formed of various substances are stacked in plural layers. In this case, the measurement of a thickness of each member placed within the article requires preparing a slice of the article as a specimen and observing a cross-section of the specimen with an optical microscope or an electron microscope. However, the preparation and the observation of the specimen from pre-shipment goods, e.g., a semiconductor chip, a printed substrate, a battery and the like, entails significant loss in terms of time and cost. Thus, a method of testing an article in a nondestructive manner has been in demand.

However, a conventional testing method using X-rays requires a reference specimen as described above. In addition, the testing method requires a technique for accurately irradiating the X-rays to the specimen based on design diagrams of the semiconductor chip, the printed substrate, the battery and the like, while such a technique has not been developed. This makes it difficult to enhance throughput of testing.

SUMMARY

Some embodiments of the present disclosure provide an X-ray nondestructive testing device which is capable of easily measuring a thickness of a measurement target object at low cost using a simple apparatus and a simple operational process.

According to one embodiment of the present disclosure, there is provided an X-ray nondestructive testing device which irradiates X-rays to an article, measures transmission amounts of the X-rays passed through the article and obtains a thickness of a measurement target object based on the transmission amounts, the article being fabricated based on a pre-stored design information and including a substrate having a predetermined X-ray absorption coefficient and the measurement target object disposed within the substrate and having another X-ray absorption coefficient differing from that of the substrate, the device including: an X-ray source configured to irradiate the X-rays to the article; a detector configured to detect the transmission amounts of the X-rays passed through the article at at least paired different locations specified in the article; a detection position specifying designator configured to specify the paired different locations as a set of paired locations based on the pre-stored design information such that a difference between transmission paths of the X-ray at the paired locations specified in the article is defined as the measurement target object; a driving mechanism configured to move the detector to the set of paired locations specified by the detection position specifying designator; and an operation calculator configured to calculate the thickness of the measurement target object based on the transmission amounts of the X-rays detected by the detector.

According to the present disclosure, it is possible to test, with respect to an article such as an electronic substrate, a wafer or the like, which is provided with a plurality of members made of various substances, a thickness of a target member among the plurality of members, a depth from a front surface of the article to the target member and the like in a nondestructive manner. Further, even if the article has a structure in which the plurality of members is stacked in plural layers, it is possible to perform the test at low cost using a simple apparatus and a simple operational process, thus accurately measuring a thickness of the target member placed within the article.

DETAILED DESCRIPTION

Some embodiments of the present disclosure will now be described in detail with reference to the accompanying drawings.

Method of Measuring Thickness of Article Using X-Rays

Figure 14:
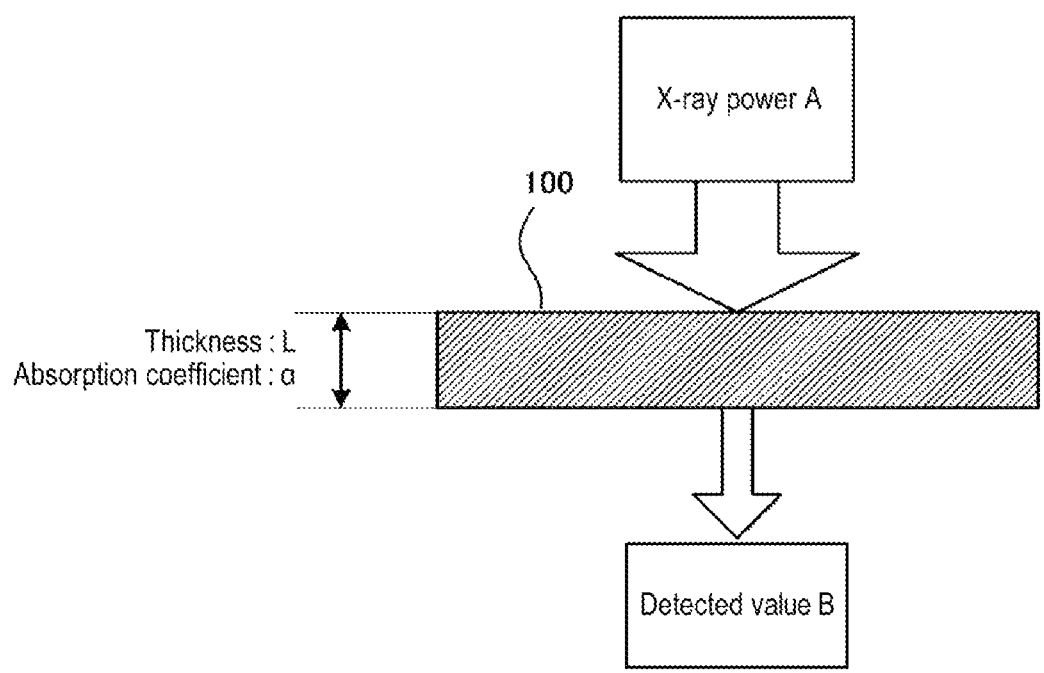
FIG. 14 is a view showing one method of measuring a thickness of an article using X-rays.

First, FIG. 14 is a view showing one method of measuring a thickness of an article using X-rays. As shown in FIG. 14, when an article 100 having a thickness L and an absorption coefficient α is irradiated with X-rays having an output A, a transmission amount of the X-rays passed through the article 100 at a detection location is defined as B. Here, the following relation is established between the thickness L, the output A, and the amount B:

$$B = A \cdot \exp(-\alpha \cdot L).$$

In addition, based on the absorption coefficient α, the output A and the amount B of the article 100, the thickness L can be calculated by the following formula:

$$L = (-1/\alpha) \cdot \log(B/A)$$

According to another method of measuring a thickness of an article, the thickness L of the article 100 can be calculated based on transmission amounts of the X-rays both when passed through the article 100 and when not passed through the article 100.

Figure 15:
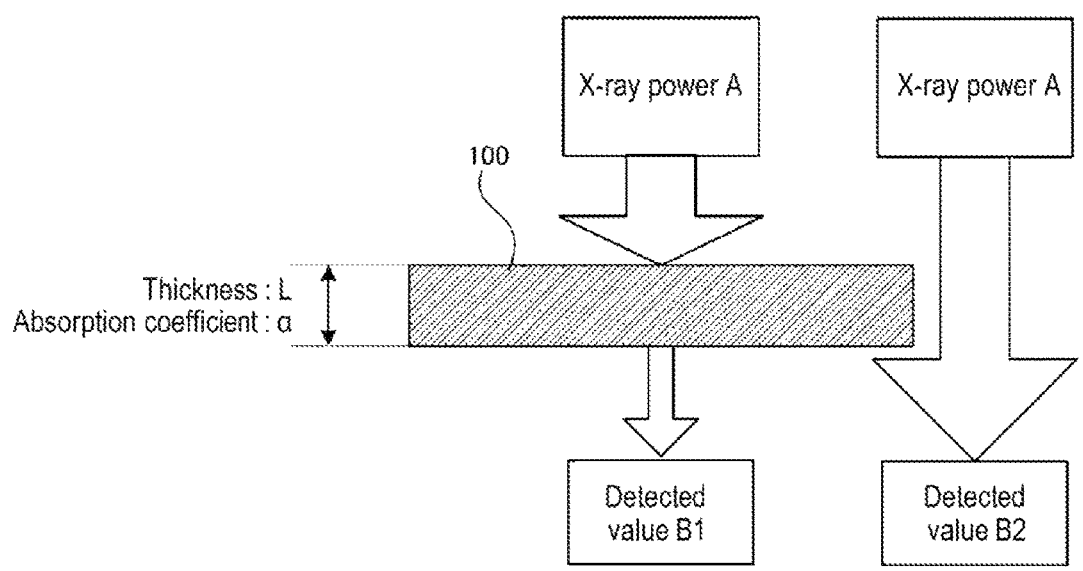
FIG. 15 is a view showing another method of measuring a thickness of an article using X-rays.

FIG. 15 is a view showing another method of measuring a thickness of an article using X-rays. As shown in FIG. 15, when the article 100 having the thickness L and the absorption coefficient α is irradiated with X-rays having the output A, a transmission amount of the X-rays passed through the article 100 at a detection location is defined as B1. In addition, when the X-rays having the output A are irradiated in the absence of the article, a transmission amount of the X-rays detected at a position corresponding to the detection position of the transmission amount B1 is defined as B2.

Here, the following relations are established:

$$B1 = A \cdot \exp(-\alpha \cdot L)$$

$$B2 = A$$

Thus, $B1/B2 = A \cdot \exp(-\alpha \cdot L)/A = \exp(-\alpha \cdot L)$.

From these formulas, the thickness L is derived by the following formula:

$$L = (-1/\alpha) \cdot \log(B1/B2).$$

Further, various methods and devices are known which measure a thickness of an article using X-rays. As an example, Japanese Laid-Open Patent Publication No. Showa 53-3262 discloses a technique for measuring a thickness L of a substance, which includes: measuring a reference transmission amount of X-rays in the absence of an article and a transmission amount of X-rays in the presence of the article, respectively; and calculating a thickness of a measurement target object based on the measured transmission amounts.

A claim of Japanese Laid-Open Patent Publication No. Showa 58-62508 discloses a technique for measuring a thickness of the measurement target object by disposing a reference object and the measurement target object between a radiation source and a radiation detector.

Japanese Laid-Open Patent Publication No. Showa 60-194304 discloses a technique which includes irradiating γ-rays having plural types of energy to measure measurement target objects having a multilayer internal structure; measuring amounts of the energy transmitted through the measurement target objects; and measuring a thickness of each of the measurement target objects based on the measured results.

Japanese Laid-Open Patent Publication No. Heisei 10-325714 discloses a technique which includes: modifying a temperature distribution obtained by calculating a heat transfer of a casting piece with solidus lines and liquidus lines which are obtained from a transmission rate of radioactive rays having different energy spectra; modifying the temperature distribution of the casting piece in a longitudinal direction to obtain a three-dimensional temperature distribution; and measuring a crater end, i.e., a thickness of a measurement target object placed within an article.

Japanese Laid-Open Patent Publication No. Heisei 7-43320 discloses a technique which includes: moving an XY stage to test, with respect to a test specimen, only a region in which a wiring pattern is formed, based on design information in which a wiring information of a wiring (circuit) pattern substrate is stated (Paragraphs 0037 to 0038); irradiating X-rays to the test specimen to obtain a constant X-ray transmission image from the test specimen (Paragraph 0027); and calculating a thickness of the test specimen (Paragraphs 0045 to 0046).

Japanese Laid-Open Patent Publication No. 2000-249532 discloses an X-ray testing method which includes: irradiating two kinds of X-rays having different wavelength distributions to a test object so as to pick up two X-ray images; calculating a difference between the two X-ray images; extracting a certain substance included in the test object from the X-ray images based on the difference; comparing the calculated difference with another difference which is obtained between an image of the certain substance and an image of a reference specimen made of the same substance as the certain substance having a predetermined thickness; and measuring a thickness of the certain substance.

Japanese Patent Untested Publication No. 2008-268076 discloses a nondestructive identification method which includes: picking up transmission images of a respective reference specimen and a test object with a first energy irradiated from a ray source while sequentially adding reference specimens having a predetermined thickness and formed of a predetermined substance; picking up transmission images of the respective reference specimen and the test object with a second energy irradiated from the ray source and different from the first energy while sequentially adding the reference specimens; calculating a relationship between a thickness of the reference specimen and a brightness of transmitted radioactive rays when the first energy and the second energy are used; and estimating a substance and thickness of the test object based on the relationship.

These methods and configurations of the devices can be suitably applied to some embodiments of the present disclosure.

First Embodiment

Figure 1:
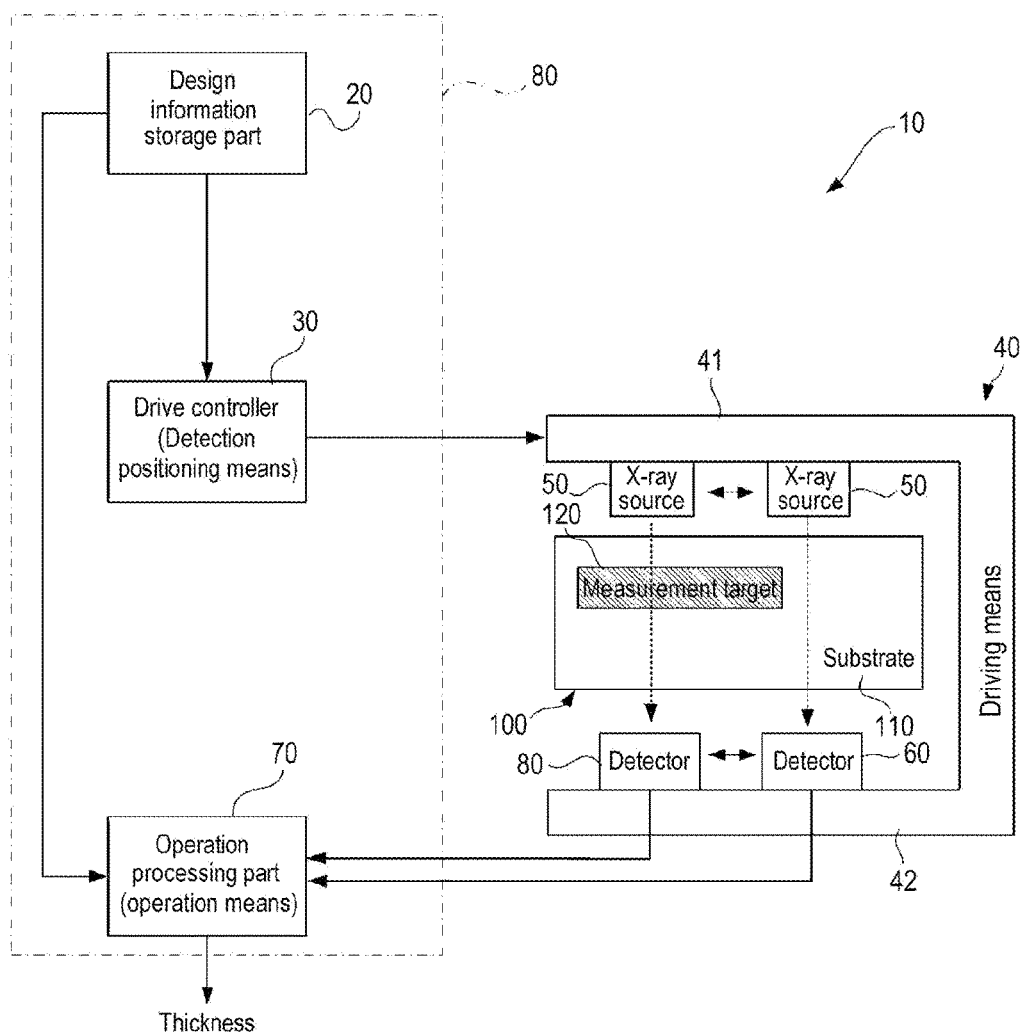
FIG. 1 is a schematic view of an X-ray nondestructive testing device according to one embodiment of the present disclosure.

FIG. 1 is a schematic view of an X-ray nondestructive testing device according to one embodiment of the present disclosure. The X-ray nondestructive testing device 10 according to the embodiment of the present disclosure is applied to a testing device of finally testing a target article, e.g., a pre-shipment wafer substrate, a pre-shipment film substrate with electronic circuits formed thereon, a build-up multilayer printed substrate, a multilayer printed circuit substrate, or the like. Hereinafter, the wafer substrate or the film substrate will be described as an example of the target article.

The X-ray nondestructive testing device 10 according to the embodiment of the present disclosure includes an X-ray source 50 configured to irradiate X-rays to an article 100, and a detector 60 used as a detection means which is configured to detect the X-rays transmitted through the article 100. Any devices known in the art may be used as the X-ray source 50 and the detector 60. Further, the X-ray nondestructive testing device 10 includes a driver 40 configured to move the X-ray source 50 and the detector 60 to a predetermined location. Further, the X-ray nondestructive testing device 10 includes a design information storage part 20 to store design information of the article 100, a driving control part 30 used as a detection position specifying designator and configured to control an operation of the driver 40, and an operation processing part 70 used as an operation calculator configured to determine a thickness of a measurement target object 120 placed within the article 100 based on a detection result obtained at the detector 60 and the design information provided from the design information storage part 20.

The driver 40 includes an X-ray source driving part 41 configured to drive the X-ray source 50 and a detector driving part 42 configured to drive the detector 60. The driver 40 is controlled by the driving control part 30 and drives the X-ray source 50 and the detector 60 in a synchronized manner such that the detector 60 detect the X-rays irradiated from the X-ray source 50. The article 100 is placed at a central location of a stage (not shown).

The article 100 is fabricated based on predetermined design information. The design information is stored in the design information storage part 20. The article 100 includes one or plural members disposed within a substrate 110. An example of the substrate 110 includes a silicon wafer substrate or a film substrate. Examples of the members disposed within the substrate 110 include various types of electronic elements, various types of functional layers made of a substance different from that of the substrate, wirings, or the like. In the X-ray nondestructive testing device 10 according to the embodiment of the present disclosure, among the members disposed within the substrate 110, a member whose thickness is unknown is defined as the measurement target object 120. The thickness of the measurement target object 120 is calculated by the operation processing part 70.

In the embodiment shown in FIG. 1, the measurement target object 120 is disposed within the substrate 110. In addition, within the substrate 110, the measurement target object 120 is disposed in a single layer or in plural layers which are stacked in the same region.

Further, the article 100 is not limited to the wafer substrate or the film substrate, and any articles may be used as long as they are subjected to a nondestructive test. That is to say, the X-ray nondestructive testing device 10 may be applied in various applications such as inspecting foreign matter in food, inspecting rust or corrosion of steel bars in construction, inspecting foreign matter such as a surgery instrument incorporated into the human body, and bench-testing a personal computer, a cellular phone, a mobile phone, a digital camera, a fuel cell, or the like.

The design information storage part 20, the driving control part 30 and the operation processing part 70 constitute a computer system 80 which is provided with a central processing unit (CPU), a read-only-memory (ROM), a random access memory (RAM), a hard disk drive (HDD), and the like. The operation processing part 70 executes programs stored in the HDD, the ROM and the like using the CPU so as to realize respective functions of the design information storage part 20, the driving control part 30, and the operation processing part 70.

The design information storage part 20 is set in a storage area of the operation processing part 70 such as the HDD. The design information storage part 20 stores, as the design information, information including a design diagram, a circuit diagram or a circuit cross-section diagram. In addition, the design information storage part 20 stores X-ray absorption coefficients of the article 100, the substrate 110 constituting the article 100, and the members included in the substrate.

The driving control part 30 sets locations at which the X-ray source 50 and the detector 60 are disposed. That is to say, the driving control part 30 specifies a pair of different locations in the article 100 as the locations at which the X-ray source 50 and the detector 60 are disposed, and determines the pair of different locations as a set of paired locations such that a difference between transmission paths of the X-rays at the pair of different locations is defined as the measurement target object 120. Information of the set of paired locations is obtained from the design information storage part 20 and is stored in, e.g., a storage means (the HDD or the RAM of the computer system 80) of the driving control part 30. Further, while in this embodiment, one X-ray source 50 is paired with one detector 60, a plurality of X-ray sources 50 may be moved to predetermined locations and a plurality of detectors 60 may be moved to locations corresponding to the predetermined locations in synchronism with the movement of the X-ray sources 50 such that transmission amounts of the X-rays can be simultaneously detected at the respective locations. In this way, the driving control part 30 sets one set or plural sets of paired locations in the article 100.

That is to say, based on the design information of the article 100 stored in the design information storage part 20, the driving control part 30 specifies a set of paired locations in the article 100 based on parameters such as the number of layers constituting the article 100, the number of layers formed between a front surface of the article 100 and the measurement target object 120 or the number of layers formed between a rear surface of the article 100 and the measurement target object 120, a region in which stacked members are present, a region in which no measurement target object is present, data representing whether a gap (distance) between the region in which the measurement target object 120 is present and the region in which no measurement target object is present is equal to or small than a predetermined distance, or the like.

The operation processing part 70 calculates a thickness of the measurement target object 120 based on transmission amounts of X-rays detected by the detector 60 at the paired locations. This calculation is performed using a known X-ray absorption formula. Using such a formula, the operation processing part 70 compares the transmission amounts of X-rays detected at the set of paired locations and calculates the thickness of the measurement target object based on a predetermined X-ray absorption coefficient of the measurement target object, the measured thickness, and the like. In addition, the operation processing part 70 calculates a thickness (distance) of the member included in the article 100.

Assuming that the article 100 having a thickness L and an absorption coefficient $\alpha$ is irradiated with X-rays having an output A and a detected transmission amount of the X-rays passed through the article 100 is defined as B, a relational formula $B=A\cdot\exp(-\alpha\cdot L)$ is established between the thickness L, the output A and the amount B. The above calculations are performed by substituting the absorption coefficient $\alpha$, the output A and the detection amount B in the relational formula and solving for the thickness L.

Next, a measurement process performed in the X-ray nondestructive testing device 10 will be described. The X-ray nondestructive testing device 10 can measure the thickness of the measurement target object through various procedures.

Measurement Process According to First Embodiment

Figure 2:
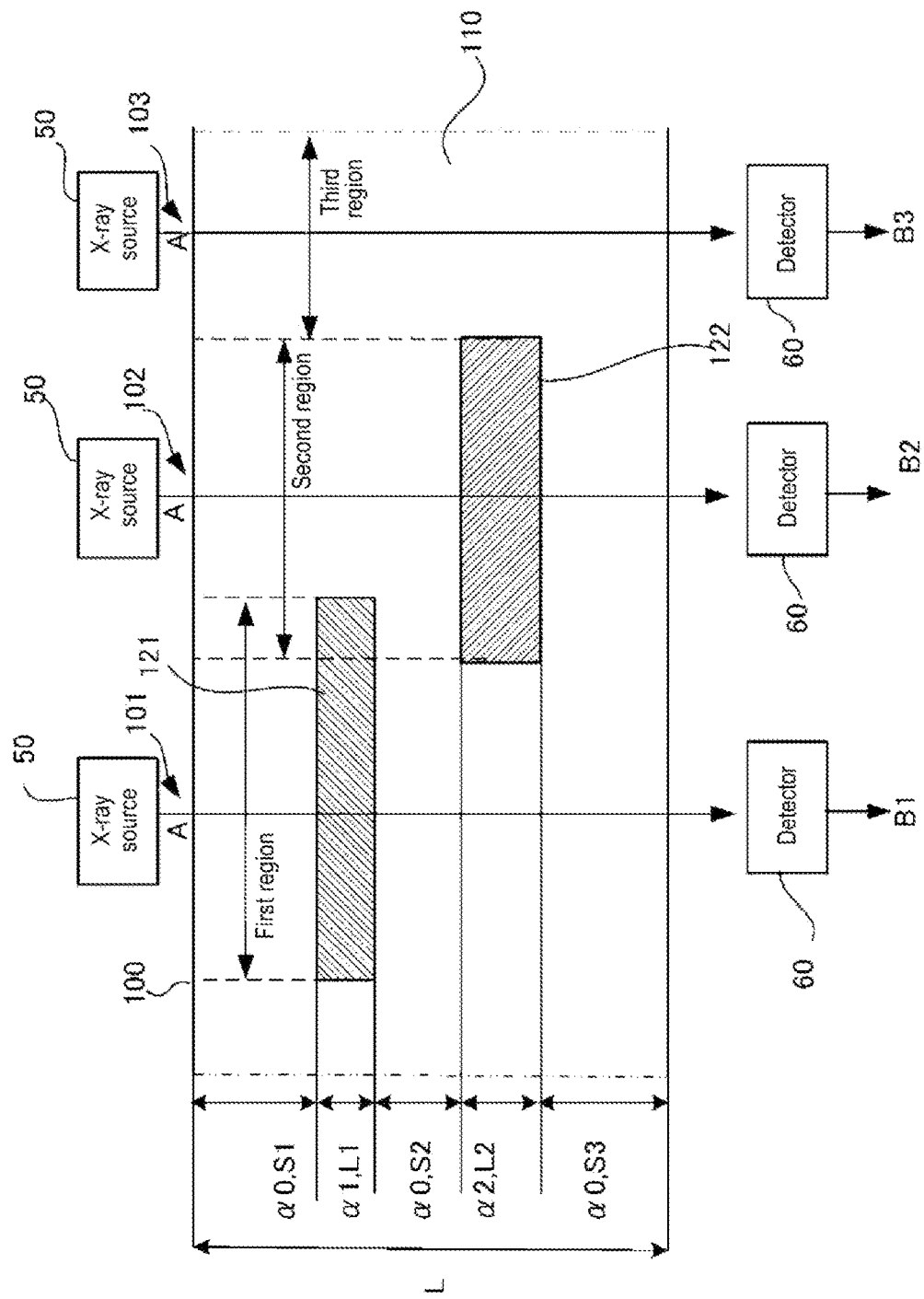
FIG. 2 is a view showing a measurement process using an X-ray nondestructive testing device according to a first embodiment of the present disclosure.

First, the measurement process according to a first embodiment will be described. FIG. 2 is a view showing the measurement process performed in the X-ray nondestructive testing device 10 according to the first embodiment of the present disclosure. Two measurement target objects, i.e., a first measurement target object 121 and a second measurement target object 122, are disposed within the substrate 110 of the article 100. Here, a transmission rate $\alpha 0$ of the substrate 110, a transmission rate $\alpha 1$ of the first measurement target object 121, and a transmission rate $\alpha 2$ of the second measurement target object 122 are predetermined values. These transmission rates are stored in the design information storage part 20.

First, the driving control part 30 specifies two different locations in the article 100 such that a difference between transmission paths of the X-ray at the two different locations is defined as the first measurement target object 121. In this embodiment, a first location 101 is selected from a first region in which the first measurement target object 121 is disposed, a second location 102 is selected from a second region in which the second measurement target object 122 is disposed, and a third location 103 is selected from a third region in which no measurement target object is disposed. The first location 101 and the third location 103 are defined as a first set of paired locations, and the second location 102 and the third location 103 are defined as a second set of paired locations.

Subsequently, the driving control part 30 controls the driving means 40 to sequentially move a pair of the X-ray source 50 and the detector 60 to the first location 101, the second location 102 and the third location 103 such that the detector 60 detects transmission amounts of the X-rays at the respective locations. In addition, the X-ray source 50 irradiates the X-rays having a predetermined output (e.g., the output A) to the article 100 and the detector 60 measures the transmission amounts of the X-rays at the respective locations. In some embodiments, plural pairs of the X-ray source 50 and the detector 60 may be installed at the respective locations such that the detector 60 of each pair measures a transmission amount at the respective location.

Assuming that the output of the X-ray source 50 is defined as A, and transmission amounts of X-rays detected by the detector 60 at the locations 101, 102 and 103 are defined as B1, B2, and B3, respectively. Based on these values, the operation processing part 70 obtains thicknesses L1 and L2 of the first and second measurement target objects 121 and 122, respectively.

Assuming that a distance from a front surface of the substrate 110 to a front surface of the first measurement target object 121 is defined as S1, a thickness of the first measurement target object 121 is defined as L1, a distance from a rear surface of the first measurement target object 121 to a front surface of the second measurement target object 122 is defined as S2, a thickness of the second measurement target object 122 is defined as L2, and a distance from a rear surface of the second measurement target object 122 to a rear surface of the substrate 110 is defined as S3, L1 can be calculated based on a ratio of B1 to B3, and L2 can be calculated based on a ratio of B2 to B3. That is to say, the following formulas are established.

$$B1/B3=\exp(-L1(\alpha 1-\alpha 0))$$

$$B2/B3=\exp(-L2(\alpha 2-\alpha 0))$$

The operation processing part 70 solves these formulas with respect to L1 and L2 to obtain their roots. As described above, in the first embodiment, the thicknesses L1 and L2 of the first measurement target object 121 and the second measurement target object 122 can be derived by a simple operation of measuring attenuation rates of the X-rays at three locations 101, 102, and 103.

Measurement Process According to Second Embodiment

Figure 3:
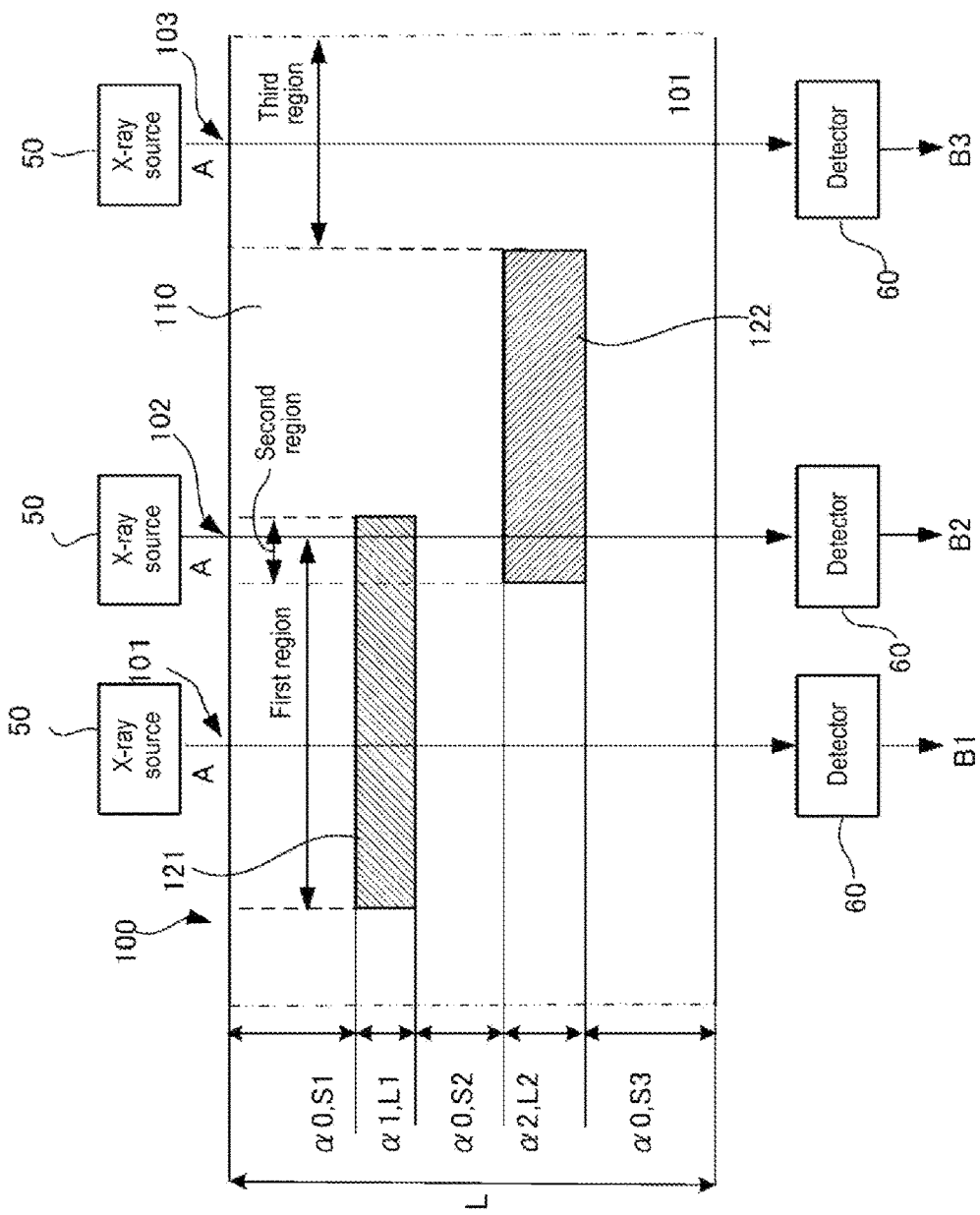
FIG. 3 is a view showing a measurement process using an X-ray nondestructive testing device according to a second embodiment of the present disclosure.

Next, a measurement process according to a second embodiment will be described. FIG. 3 is a view showing the measurement process performed by the X-ray nondestructive testing device 10 according to the second embodiment of the present disclosure. In the second embodiment, the driving control part 30 selects, in the article 100, a first location 101 from a first region in which the first measurement target object 121 is present, a second location 102 from a second region in which the first measurement target object 121 overlaps with the second measurement target object 122, and a third location 103 from a third region in which no measurement target object is present. In addition, the driving control part 30 specifies a pair of the third location 103 and the first location 101 as a first set of paired locations, and specifies a pair of the second location 102 and the first location 101 as a second set of paired locations.

Subsequently, the driving control part 30 controls the driving means 40 to sequentially move the pair of the X-ray source 50 and the detector 60 to the first location 101, the second location 102 and the third location 103 such that the detector 60 detects transmission amounts of the X-rays at the respective locations. Thus, the values B1, B2 and B3 are obtained.

Thereafter, the operation processing part 70 calculates the thickness L1 of the first measurement target object 121 using a ratio of B1 to B3 which are obtained at the first set of the third location 103 and the first location 101. Similarly, the operation processing part 70 calculates the thickness L2 of the second measurement target object 122 using a ratio of B1 to B2 which are obtained at the second set of the second location 102 and the first location 101. Here, a transmission rate α0 of the substrate 110, a transmission rate α1 of the first measurement target object 121, and a transmission rate α2 of the second measurement target object 122 are predetermined values.

Measurement Process According to Third Embodiment

Figure 4:
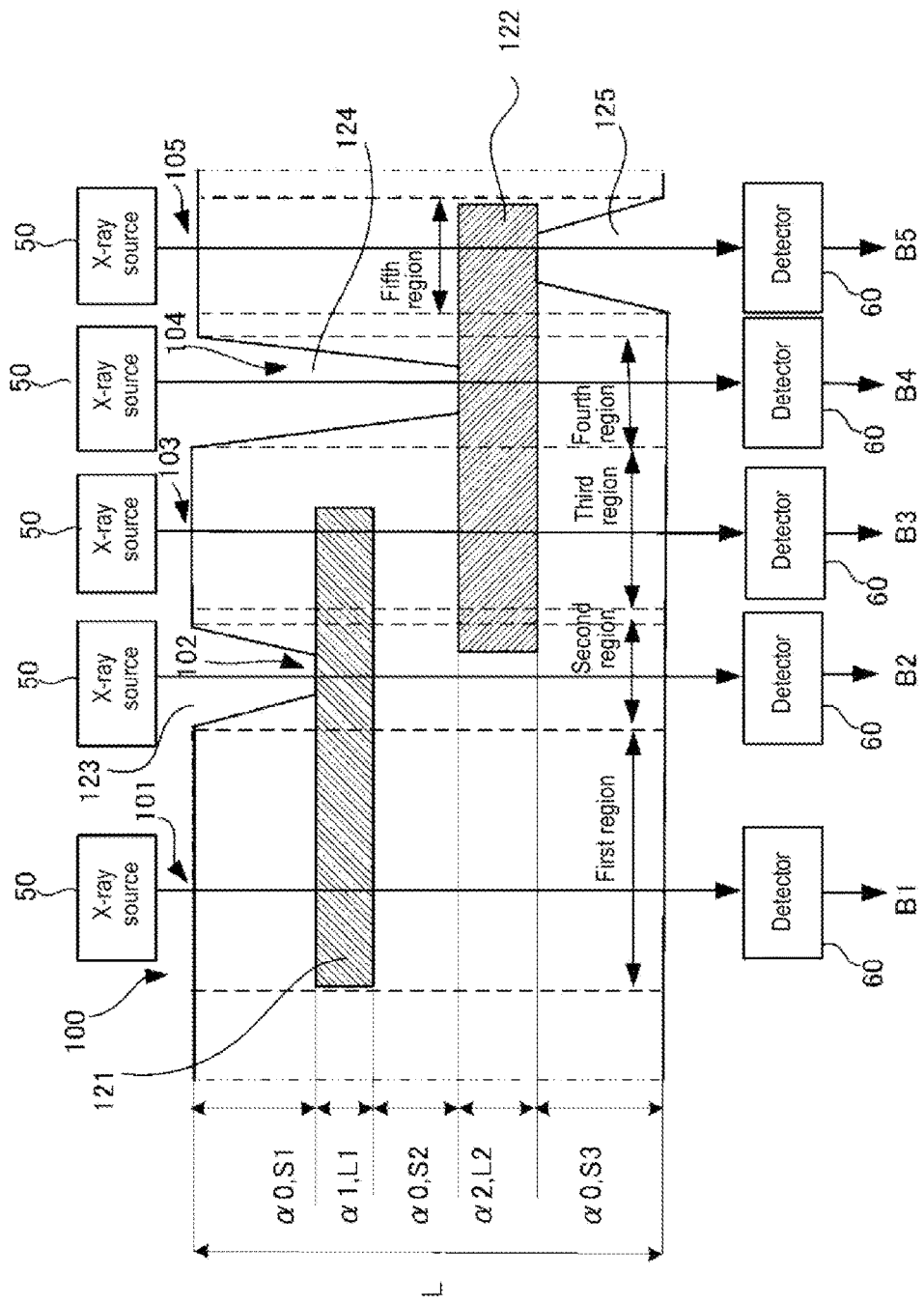
FIG. 4 is a view showing a measurement process using an X-ray nondestructive testing device according to a third embodiment of the present disclosure.

Next, a measurement process according to a third embodiment will be described. FIG. 4 is a view showing the measurement process performed in the X-ray nondestructive testing device 10 according to the third embodiment of the present disclosure. In the third embodiment, trenches 123, 124, 125 are formed in the substrate 110 of the article 100, in addition to the first measurement target object 121 and the second measurement target object 122.

The trench 123 is formed to extend from the front surface of the article 100 having a thickness L up to the front surface of the first measurement target object 121. The trench 124 is formed to extend from the front surface of the article 100 up to the second measurement target object 122. Trench 125 is formed to extend from the rear surface of the article 100 up to the rear surface of the second measurement target object 122. Further, a distance from the front surface of the article 100 to the front surface of the first measurement target object 121, i.e., a depth of the trench 123, is defined as S1. A thickness of the first measurement target object 121 is defined as L1. A distance (gap) between the first measurement target object 121 and the second measurement target object 122 is defined as S2. A thickness of the second measurement target object 122 is defined as L2. A distance (gap) from the second measurement target object 122 to the rear surface of the article 100, i.e., a depth of the trench 125, is defined as S3.

Further, a transmission rate α0 of the substrate 110, a transmission rate α1 of the first measurement target object 121 and a transmission rate α2 of the second measurement target object 122 are predetermined values, and L1 and L2 are also predetermined values. In some embodiments, holes may be formed in the substrate 110 as measurement target objects instead of the trenches.

In this embodiment, a portion (corresponding to a depth of the trench 123: S1) formed to extend from the front surface of the article 100 to the front surface of the first measurement target object 121, a portion (corresponding to a depth of the trench 124: S1+L1+S2) formed to extend from the front surface of the article 100 to the front surface of the second measurement target object 122, and a portion (corresponding to a depth of the trench 125: S3) formed to extend from the rear surface of measurement target object 122 to the rear surface of the article 100 are set as measurement target objects. Such setting is similar to obtaining the dimensions S1, S2, S3. Through these dimensions, the depths of the trenches 123, 124 and 125 can be obtained.

To do this, the driving control part 30 specifies the following five locations, as shown in FIG. 4.

First location 101: selected from a first region in which the first measurement target object 121 is disposed and no trench is formed, Second location 102: selected from a second region in which the first measurement target object 121 is disposed and the trench 123 is formed, Third location 103: selected from a third region in which the first measurement target object 121 and the second measurement target object 122 are disposed, Fourth location 104: selected from a fourth region in which the second measurement target object 122 is disposed and the trench 124 is formed, and Fifth location 105: selected from a fifth region in which the trench 125 and the second measurement target object 122 disposed therein is disposed.

The driving control part 30 selects three sets of paired locations as follows:

First set of paired locations: the first location 101 and the second location 102, Second set of paired locations: the third location 103 and the fourth location 104, and Third set of paired locations: the third location 103 and the fifth location 105.

In addition, the operation processing part 70 calculates thickness dimensions by the following sequence.

The dimension S1 is calculated from a ratio of a transmission rate B1 to a transmission rate B2 which are obtained at the first set of paired locations.

Subsequently, the dimension S1+L1+S2 is calculated from a ratio of a transmission rate B3 to a transmission rate B4 which are obtained at the second set of paired locations.

where, since the dimensions S1 and L1 are predetermined values, it is possible to calculate the dimension S2.

Thereafter, the dimension S3 is calculated from a ratio of the transmission rate B3 to a transmission rate B5 which are obtained at the third set of paired locations.

In this way, the dimensions S1, S2 and S3 can be calculated, in addition to the dimensions L1 and L2 which are the predetermined values.

Modified Example of Measurement Process According to Third Embodiment

Next, a modified example of the measurement process according to the third embodiment will be described. In this modified example, the thickness L1 of the first measurement target object 121, the thickness L2 of the second measurement target object 122 and the total thickness L of the article 100 are predetermined values. Each of the dimensions S1, S2 and S3 is obtained as in the above embodiment using the total thickness L. Further, in this case, the first set of paired locations (the first location 101 and the second location 102) and the second set of paired locations (the third location 103 and the fourth location 104) as described above are used as sets of measurement locations.

Then, the operation processing part 70 calculates each thickness according to the following sequence.

The dimension S1 is calculated from measurement values obtained at the first set of paired locations.

The dimension S2 is calculated from measurement values obtained at the second set of paired locations.

Using the calculated dimensions S1 and S2, and the predetermined values L, L1, and L2, the following formula is established:

$$L=S1+L1+S2+L2+S3$$

Thus, $$S3=L-(S1+L1+S2+L2)$$

In this way, it is possible to calculate the dimensions S1, S2 and S3, in addition to the predetermined values L1 and L2.

Measurement Process According to Fourth Embodiment

Next, a measurement process according to a fourth embodiment will be described. The fourth embodiment uses a design diagram as the design information of the article. In addition, in the fourth embodiment, a film substrate with an insulation layer formed therein as an article is defined as a test object of the X-ray nondestructive testing device 10. A thickness of a circuit layer formed in the insulation layer of the film substrate before shipment is measured.

Figure 5:
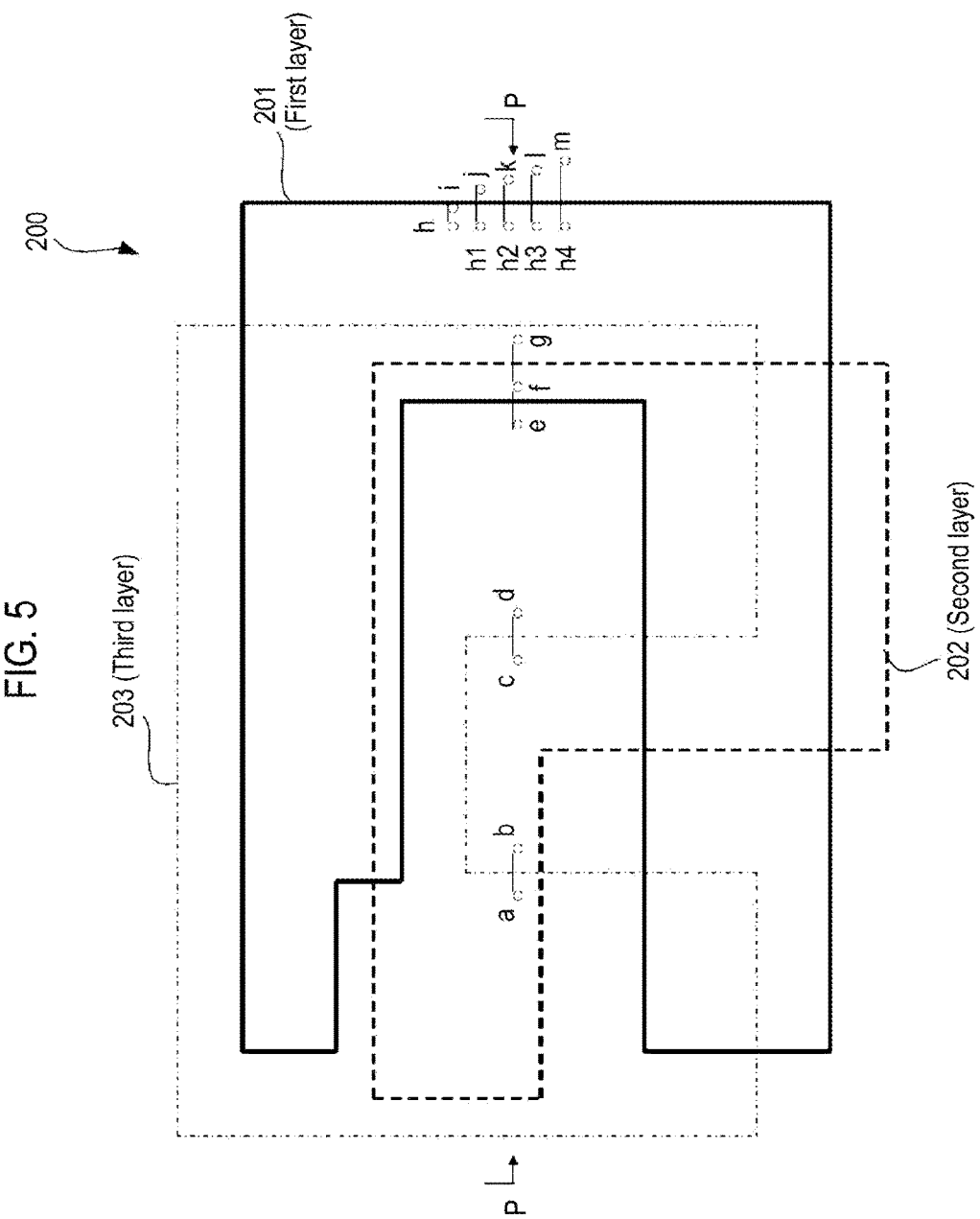
FIG. 5 is a view showing a design diagram of an article to be measured in an X-ray nondestructive testing device according to a fourth embodiment of the present disclosure.
Figure 6:
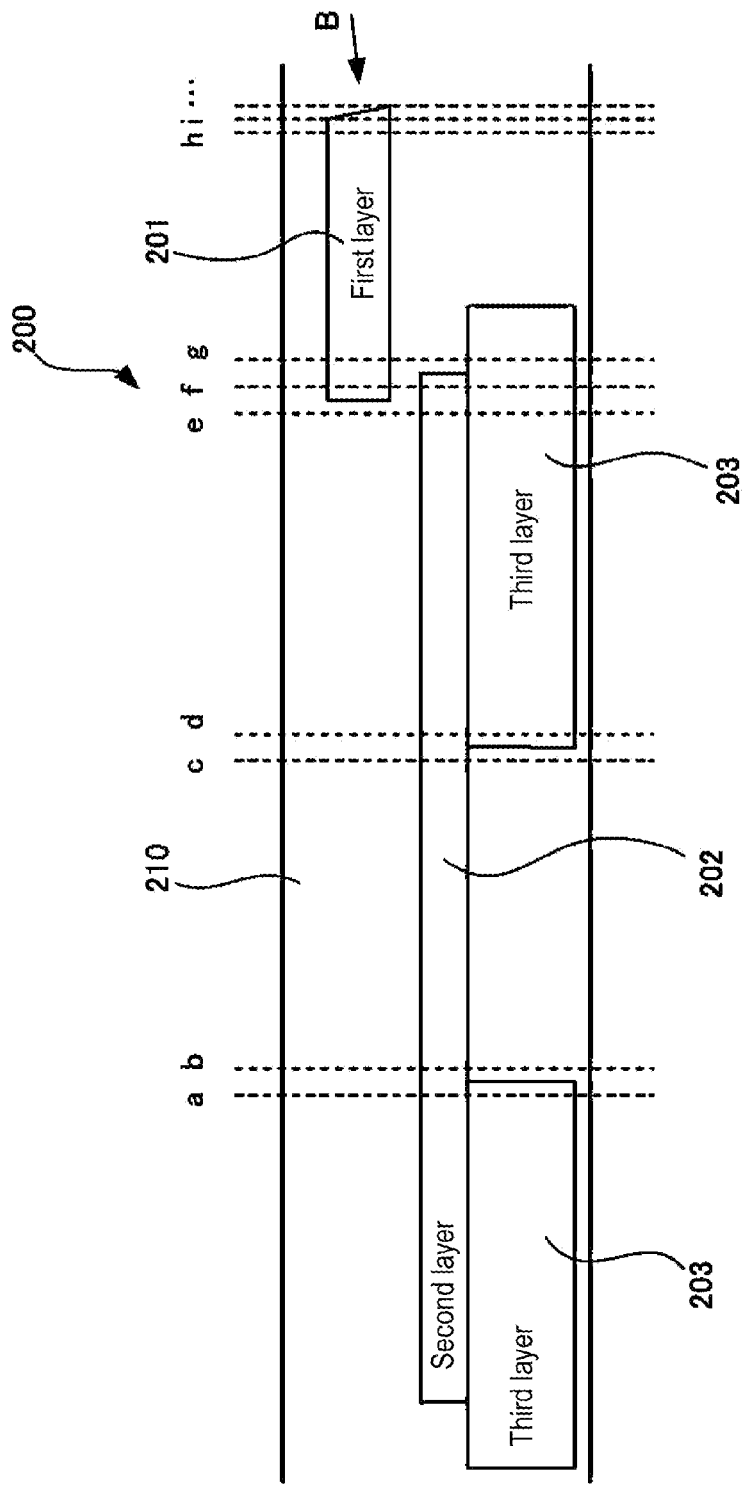
FIG. 6 is a sectional view taken along line P-P of FIG. 5, which shows the design diagram of the article to be measured in the X-ray nondestructive testing device according to the fourth embodiment of the present disclosure.
Figure 7:
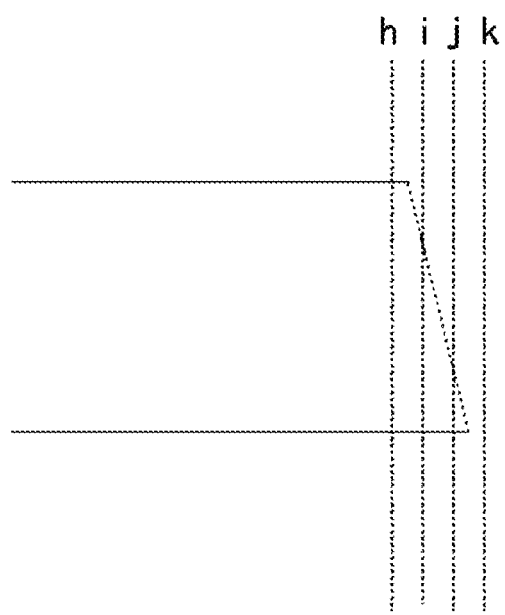
FIG. 7 is an enlarged view of Part B of FIG. 6.

FIG. 5 is a view showing a design diagram of a film substrate used as a test object in the X-ray nondestructive testing device according to the fourth embodiment of the present disclosure. FIG. 6 is a sectional view taken along line P-P in the design diagram of the film substrate shown in FIG. 5. FIG. 7 is an enlarged view of a portion B in FIG. 6. A film substrate 200 includes a plurality of circuit layers including first layer 201 (indicated by a solid line in FIG. 5), a second layer 202 (indicated by a dash line in FIG. 5) and a third layer 203 (indicated by a dash-dot line in FIG. 5). Further, a thickness of the first layer 201 is a predetermined value.

The film substrate 200 is fabricated based on design information shown in FIG. 5 and FIG. 6. The X-ray nondestructive testing device 10 specifies a set of paired different locations in the film substrate 200, at which a difference between transmission paths of X-rays is defined as a measurement target object. The X-ray nondestructive testing device 10 detects transmission amounts of the X-rays at the set of paired different locations, and compares the detected transmission amounts with each other. Thus, the thickness of the circuit layer formed in the insulation layer is measured.

The X-rays are irradiated to pass through locations a, b, c, d, e, f, g, h, i, . . . specified in the film substrate 200 and transmission amounts of the X-rays at the respective locations are measured. In FIG. 5, the locations at which the X-ray source 50 and the detector 60 are disposed are indicated by small circles with symbols a, b, c, d, e, f, g, h, i, . . . . The X-rays are transmitted in a direction perpendicular to the drawing at each of the locations. In addition, in FIG. 5, a set of paired locations through which the X-rays transmit, are shown to be connected by a line. Further, in FIG. 6, transmission paths of the X-rays are indicated by dotted lines.

Further, in the fourth embodiment, locations which are represented by paired symbols such as a-b, c-d, e-f, f-g, h-i, h-j, h-k, . . . , are defined as a set of measurement locations, respectively.

In the insulation layer 210 of the film substrate 200, the circuit layer including the three layers 201, 202, 203 is formed. A difference between values detected at the paired locations a-b and a difference between values detected at the paired locations c-d are caused by the presence of the third layer 203. Thus, a thickness of the third layer 203 can be calculated from the transmission amounts of the X-rays detected at each of the paired locations a-b and c-d, and a predetermined absorption coefficient of the third layer 203. Thus, it is possible to check whether the article is fabricated to have a suitable thickness before shipment. The calculation of the thickness is performed in the same manner as in the first, second and third embodiments described above.

Likewise, a difference between values detected at the paired locations e-f is caused by a thickness of the first layer 201 and a distance (gap) between the first layer 201 and the second layer 202. Thus, it is possible to obtain the distance (gap) between the first layer 201 and the second layer 202 based on transmission amounts of the X-rays detected at the paired locations e-f and predetermined absorption coefficients of the first layer 201 and the insulation layer 210.

Further, a difference between values detected at the paired locations f-g is caused by the distance (gap) between the first layer 201 and the second layer 202 and a thickness of the second layer 202. Thus, it is possible to obtain a thickness of the third layer 203 based on transmission amounts of the X-rays detected at the paired locations f-g, the distance (gap) between the first layer 201 and the second layer 202 calculated in the above, and the absorption coefficient of the second layer 202.

The following is a brief summary as to a layer structure obtained at the locations c, d, e, f and g.

c (the same as b): the second layer 202 d (the same as a): the second layer 202+ the third layer 203 e: the second layer 202+ the third layer 203 f: the first layer 201+ the distance (gap) between the first layer 201 and the second layer 202+ the second layer 202+ the third layer 203 g: the first layer 201+ the distance (gap) between the first layer 201 and the third layer 203+ the third layer 203

Accordingly, the thickness of the third layer 203 is calculated at the paired locations c-d. The distance (gap) between the first layer 201 and the second layer 202 is calculated at the paired locations e-f based on the calculated thickness of the third layer 203 and the predetermined thickness of the first layer 201. The thickness of the second layer 202 is calculated at the paired locations f-g based on the calculated distance (gap) between the first layer 201 and the second layer 202.

As described above, according to this embodiment, the driving control part 30 calculates a thickness of an unknown layer based on a calculated thickness of a certain layer, which makes it possible to determine all combinations which can be obtained by sequentially specify another sets of paired locations. This process can determine an optimal combination within at most a range from 10 μm to several tens of millimeters. The detector sequentially detects transmission amounts of the X-rays at the paired locations constituting the optimal combination, thus sequentially obtaining thicknesses of unknown layers.

As described above, according to the fourth embodiment, it is possible to test whether the second layer 202 is formed to have a suitable thickness before shipment. Likewise, in terms of the location d (or e), the thickness of the third layer 203 is obtained by calculating a difference between a transmission amount of the X-rays detected at the location d and a transmission amount of the X-rays detected at the location c which is paired with the location d.

In this way, it is possible to sequentially obtain thicknesses of unknown layers by specifying a set of paired locations in such a manner that the thickness of the third layer 203 is calculated at another location (or layer) as a starting location at which a thickness of a measurement target object is not obtained, and consequently, the thickness of the second layer 202 is calculated.

In some embodiments, it is possible to sequentially obtain thicknesses of unknown layers by specifying a set of paired locations and sequentially detecting transmission amounts of the X-rays using the detector at the set of paired locations, such a manner that the thickness of the third layer 203 is calculated at another location (or layer) as a starting location at which a thickness of a measurement target object is not obtained, and consequently, the thickness of the second layer 202 is calculated.

Modified Example of Measurement Process According to Fourth Embodiment

Next, a modified example of the measurement process according to the fourth embodiment will be described. This modified example is to measure a cross-sectional shape of a contour of a layer formed in the article 100 using the X-ray nondestructive testing device 10. As shown in FIG. 5, when a border line is defined between an inner region in which a layer including a measurement target object (e.g., the first layer 201) is present and an outer region in which a layer including no measurement target object (e.g., the first layer 201) is present, two locations h and i selected from the inner region are defined as a set of paired locations (h-i); a location h1 selected from the inner region and a location j selected from the border line are defined as a set of paired locations (h1-j); a location h2 selected from the inner region and a location k selected from the outer region are defined as a set of paired locations (h2-k); locations h3, h4, . . . selected from the inner region and locations l, m, . . . selected from the outer region with slivers of space in between the respective locations are defined as respective sets of paired locations (h3-l), (h4-m), . . . . The X-rays are irradiated along transmission paths h, i, . . . at the respective sets of paired locations so that transmission amounts of the X-rays passed through the respective sets of paired locations are detected. The detected transmission amounts are compared with each other, thus obtaining an inclination of the border line between the inner region in which the measurement target object (e.g., the first layer 201) is disposed and the outer region in which the measurement target object (e.g., the first layer 201) is not disposed.

From a graph which is obtained by graphically showing differences between the detected transmission amounts of the X-rays and a variation in thickness obtained at coordinates of respective locations at which the transmission amounts of the X-rays are detected, it is possible to obtain the inclination of the cross-section in the vicinity of the border line between the inner region in which the measurement target object (e.g., the first layer 201) is disposed and the outer region in which the measurement target object (e.g., the first layer 201) is not disposed, as shown in FIG. 7.

In the aforementioned measurement process, like the locations a, b, c and d described in the fourth embodiment, the driving control part 30 may set plural sets of paired locations such that a distance between two sets of paired locations in the article is relatively long, thus obtaining a thickness of the same measurement target object. This setting calculates the thickness of the measurement target object (layer) using an average amount of the X-rays while reducing errors in detecting the transmission amounts of the X-rays passed through the multilayered structure.

Alternatively, the driving control part 30 may set plural sets of paired locations such that a distance between two sets of paired locations in the article is relatively short like the locations e, f and g. By detecting transmission amounts of the X-rays passed through these locations e, f and g, it is possible to enhance accuracy of a thickness measurement at the respective regions.

When the plural sets of paired locations are selected from regions in which the number of layers constituting the measurement target objects is small, it is possible to enhance a test throughput, thus finally checking substrates such as a lot of wafer substrates, a lot of film substrates, capacitors such as lithium ion batteries or the like, before shipment. Such an effect may be manifested in other embodiments of the present disclosure.

In addition, when the central portion of the stage is selected as a measurement location at which a transmission amount of X-rays is detected, the X-rays can be irradiated from directly above the measurement location so that a clear X-ray image is obtained, thus accurately detecting a transmission amount of the X-rays passed through the measurement location.

Further, as shown in FIG. 6, the design information may include a circuit cross-sectional diagram in addition to the circuit diagram. Based on the circuit cross-sectional diagram, a set of paired different locations can be specified in the substrate having a multilayered structure such that a difference between layers existing at the paired different locations is defined as a measurement target object. In this way, measurement locations at which the transmission amounts of the X-rays are detected are determined. The detected transmission amounts of the X-rays passed through the measurement locations are compared with each other such that a thickness of a circuit layer formed inside a resist layer is measured before shipment.

Figure 8:
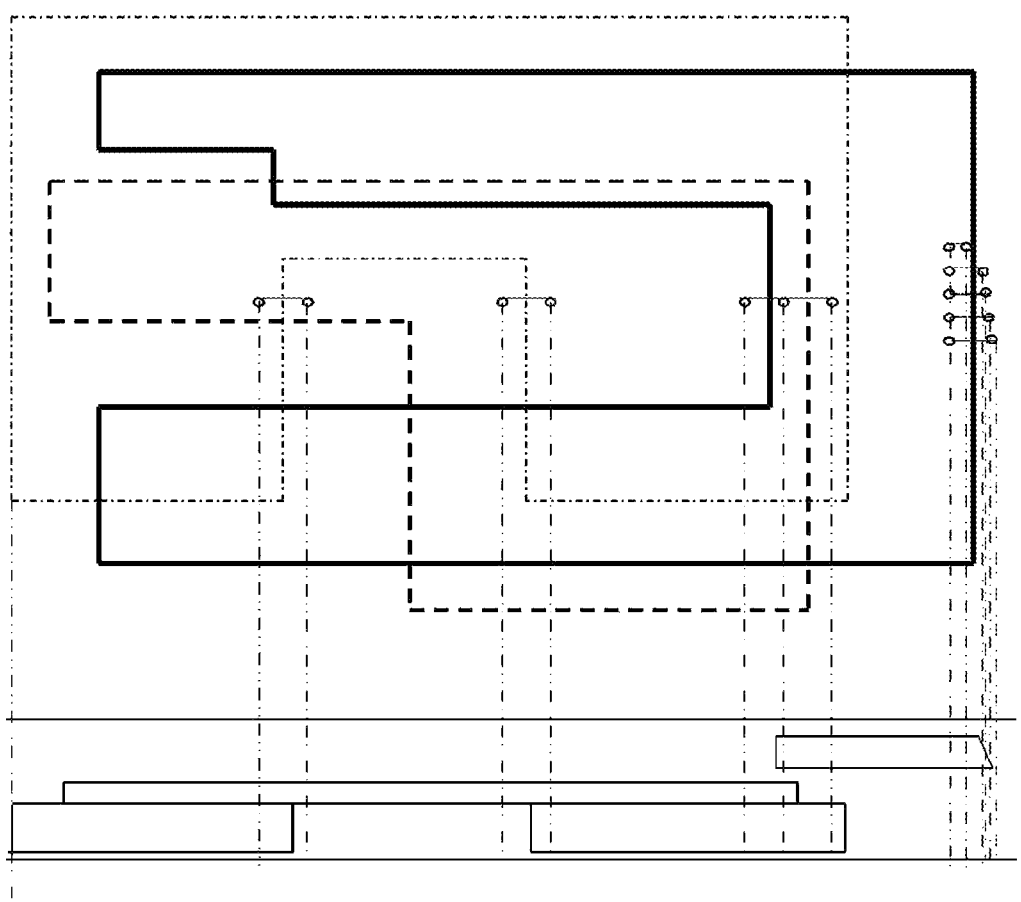
FIG. 8 is a view showing a display state of an image display device.

In some embodiments, the circuit diagram (FIG. 5) and the circuit cross-sectional diagram (FIG. 6) stored in the design information storage part 20 may be combined as shown in FIG. 8 in the measurement process such that a combined image is displayed on an image display device (not shown) of the computer system 80. With this configuration, it is possible to more conveniently manipulate the X-ray nondestructive testing device 10.

Measurement Process According to Fifth Embodiment

Figure 9:
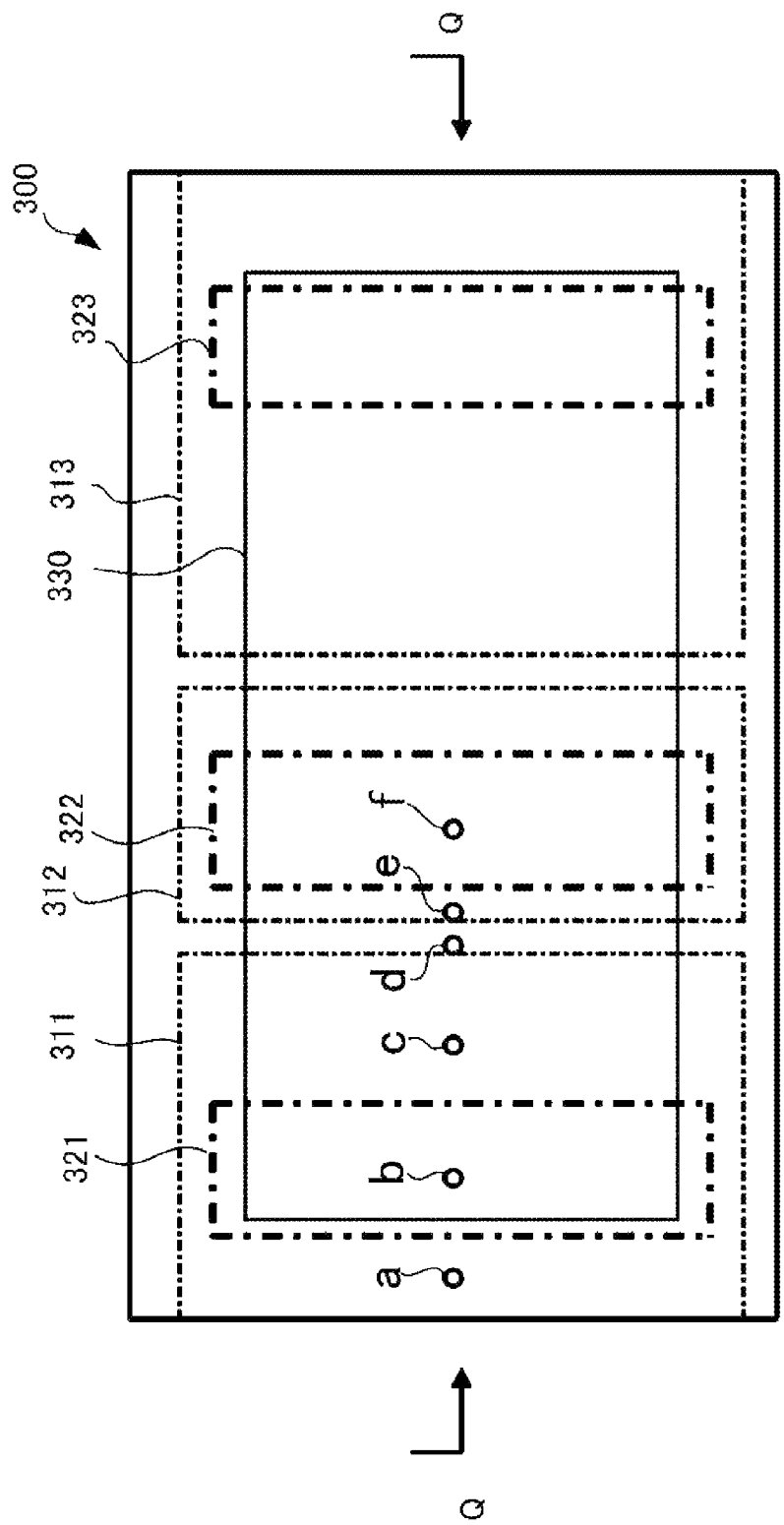
FIGS. 9A and 9B show design diagrams of an article to be measured in an X-ray nondestructive testing device according to a fifth embodiment of the present disclosure, FIG. 9A being a plan view and FIG. 9B being a sectional view taken along line Q-Q of FIG. 9A.

Next, a measurement process according to a fifth embodiment will be described. FIGS. 9A and 9B show design diagrams of an article used as a measurement target object in the X-ray nondestructive testing device 10 according to the fifth embodiment of the present disclosure, FIG. 9A being a plan view and FIG. 9B being a sectional view taken along line Q-Q of FIG. 9A. In the fifth embodiment, a substrate 300 having copper (Cu) wirings 321, 322 and 323 formed therein is provided as the measurement target object. The X-ray nondestructive testing device 10 irradiates X-rays to the substrate 300 to measure a thickness of the copper (Cu) wirings 321, 322 and 323.

Figure 10:
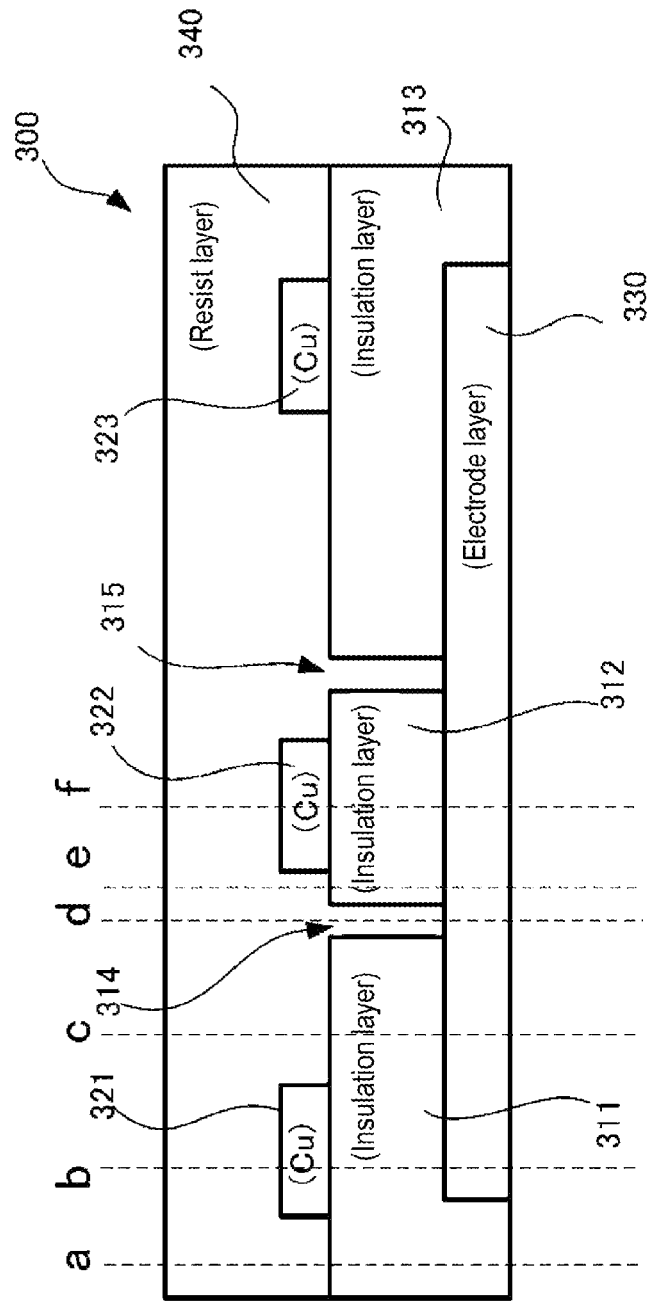
FIG. 10 is a view showing a method of measuring a transmission amount of X-rays in the fifth embodiment of the present disclosure.

Further, in the fifth embodiment, the entire substrate 300 is irradiated with the X-rays. As shown in FIG. 10, an X-ray transmission image of the substrate 300 is picked up by an image pickup device 350 as a detection means disposed below the substrate 300. The image pickup device 350 has a planar shape and is configured to pick up the X-ray transmission image of the X-rays passed through the entire substrate 300. In addition, the X-ray transmission image of the substrate 300 is outputted at a level of, e.g., 256 degrees of gradation, based on absorption amounts (transmission amounts) of the X-rays.

In the fifth embodiment, it is possible to detect a transmission amount of X-rays at a certain location in the substrate 300 based on a gradation value obtained at the certain location by the image pickup device 350.

As shown in FIGS. 9A and 9B, the substrate 300 includes a first insulation film 311 having a thickness of 18 μm, a second insulation film 312, and a third insulation film 313 formed therein. A trench 314 is formed between the first insulation film 311 and the second insulation film 312. A trench 315 is formed between the second insulation film 312 and the third insulation film 313. Further, in FIGS. 9A and 9B, the copper wiring 321 (having a thickness of 12 µm) is stacked on the first insulation film 311. The copper wiring 322 (having a thickness of 12 µm) is stacked on the second insulation film 312. The copper wiring 323 (having a thickness of 12 µm) is stacked on the third insulation film 313.

Further, an electrode layer 330 is disposed below the insulation films 311, 312 and 313. For the sake of simplicity, assume that the electrode layer 330 formed of copper has a thickness of 12 µm. Further, a solder resist (hereinafter referred to as a "resist") 340 is disposed on the insulation films 311, 312 and 313, and the wirings 321, 322 and 323.

In the fifth embodiment, a transmission amount of the X-rays is measured at each of six locations specified in the substrate 300, i.e., a, b, c, d, e and f as shown in FIGS. 9A and 9B. This measurement is realized based on the gradation values obtained by the image pickup device 350 at the respective locations.

At each of the locations a, b, c, d, e and f, the X-rays transmit through the following members.

Location a: the resist 340 and the first insulation film 311

Location b: the resist 340, the wiring 321, the first insulation film 311, and the electrode layer 330

Location c: the resist 340, the first insulation film 311, and the electrode layer 330

Location d: the resist 340, and the electrode layer 330

Location e: the resist 340, the second insulation film 312, and the electrode layer 330

Location f: the resist 340, the wiring 322, the second insulation film 312, and the electrode layer 330

Further, in FIG. 9B, paths through the X-rays that are transmitted are indicated by dotted lines, and the X-ray source 50 and the detector 60 are disposed at both sides of the respective paths. In FIG. 9A, each of the wirings 321, 322 and 323 is indicated by a thick dash-dot line, each of the insulation films 311, 312 and 313 is indicated by a dash-dot line, and the electrode layer 330 is indicated by a solid line.

In the fifth embodiment, the driving control part 30 specifies locations at which the transmission amounts of the X-rays are detected, based on the design information (e.g., the design diagram, the circuit diagram, or the like) of the substrate 300 stored in the design information storage part 20. In this case, the driving control part 30 specifies a set of paired different locations in the substrate 300 such that a difference between transmission paths of layers at the paired different locations is defined as a measurement target object. In the fifth embodiment, locations (a, c), (f, c) and (d, e) in the substrate 300 are specified as sets of paired different locations.

A difference between transmission paths at the paired locations (a-c) corresponds to the electrode layer 330, a difference between transmission paths at the paired locations (f-c) corresponds to the wiring 322, and a difference between transmission paths at the paired locations (d-e) corresponds to the second insulation film 312. Accordingly, by detecting the transmission amounts of the X-rays at each of the locations a, c, f, c, d and e using the detector 60, it is possible to obtain a thickness of each of the electrode layer 330, the insulation films 311, 312 and 313, and the resist 340 based on respective differences between the detected transmission amounts of the X-rays and an absorption coefficient of each of the layers or the films.

Further, a pair of two different locations, i.e., one location selected from a region in which the measurement target object (e.g., the electrode layer 330) is disposed and another location selected in the vicinity of the region are specified in the substrate 300. A thickness of the measurement target object (e.g., the electrode layer 330) is calculated by detecting transmission amounts of the X-rays at the two different regions and comparing the detected transmission amounts.

Further, the two different locations specified in the substrate 300 are selected in the vicinity of a border line between a region in which a layer including the measurement target object (e.g., the electrode layer 330) is present and a region in which a layer excluding the measurement target object (e.g., the electrode layer 330) is present.

Figure 11:
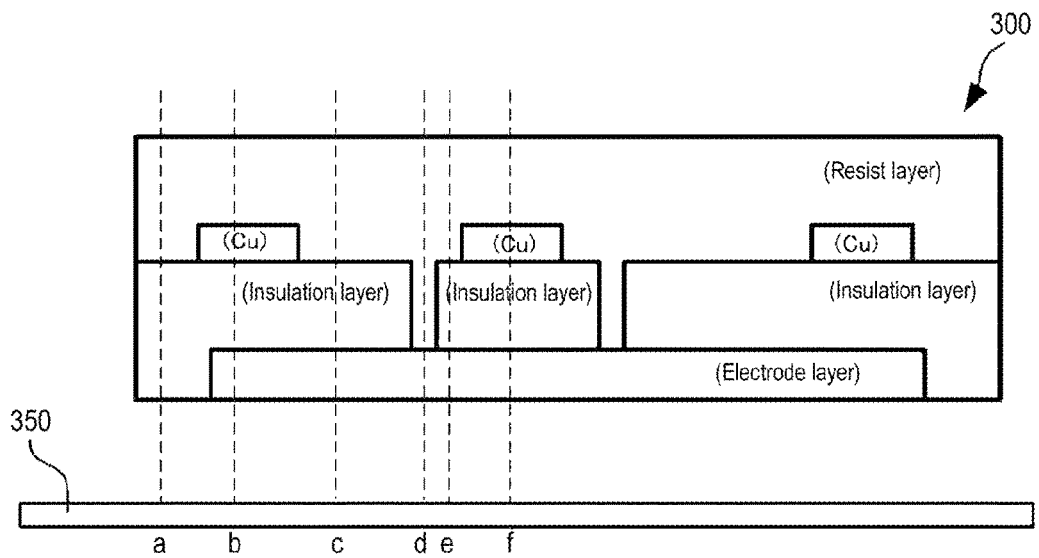
FIG. 11 shows a table showing an absorption amount and a structure in each region, which are obtained by performing a measurement process using the X-ray nondestructive testing device according to the fifth embodiment of the present disclosure.

Next, a detailed measurement process will be described. FIG. 11 is a table showing a gradation value and a layer structure in each region in the measurement process performed by the X-ray nondestructive testing device 10 according to the fifth embodiment of the present disclosure. In the fifth embodiment, the driving control part 30 performs the following calculations (1) and (2).

These calculations are performed by substituting the detected transmission amounts in the following formula and solving for the thickness L:

$$\alpha^L = B1/B2$$

wherein $\alpha$ is an attenuation rate, and B1 and B2 are X-ray transmission amounts (concentrations) in a set of respective regions (or regions).

(1) The thickness of the electrode layer 330 is calculated based on a difference between the transmission amounts of the X-rays at the set of paired locations (a-c) and an attenuation rate $\alpha C$ (=0.9814: attenuation rate per micrometer) of Cu to the X-rays.

Here, Bc/Ba=130/166=0.7831, and thus the thickness of the electrode layer 330 is 13.02 µm.

(2) Likewise, at the set of paired locations (f-c), a thickness of the second insulation film 312 is calculated according to the following calculation using the attenuation rate $\alpha C$ (=0.9814: attenuation rate per micrometer) of the X-rays at the wiring 322.

Here, Bc/Bf=96/130=0.7384, and thus the thickness of the wiring 322 is 16.15 µm.

(3) Likewise, at the set of paired locations (d-e), a thickness of the second insulation film 312 is calculated according to the following calculation using an attenuation rate $\alpha R$ (=0.9947: attenuation rate per micrometer) of the insulation films 311, 312 and 313.

Here, Be/Bd=129/143=0.9021, and thus the thickness of the insulation film 312 is 19.4 µm.

In some embodiments, although not shown, for example, a set of paired locations at which a reference X-ray transmission amount corresponding to a thickness of 10 µm is detected may be selected in a substrate. By measuring whether the X-rays are detected many times with respect to the reference X-ray transmission amount, it is possible to simply calculate a thickness of a measurement target object. Alternatively, the detector may be subjected to a calibration (correction, original point correction) process.

In some embodiments, a reference substrate into which a measurement target object having a predetermined thickness is incorporated at a predetermined depth position from a front surface of the reference substrate, or an easy-to-measurement pattern (test pattern) having a predetermined thickness, may be disposed. In this case, a thickness of the measurement target object may be easily calculated by measuring a transmission amount of X-rays and comparing the measured transmission amount with a transmission amount of the X-rays passed through an electronic circuit pattern to be measured.

According to the fifth embodiment, as shown in FIG. 10, the design information (design data) which is obtained by overlapping design diagrams corresponding to four members such as the interior (resist) of the substrate, copper (Cu) films, insulation films, and an electrode layer formed below the insulation films through a simulation, may be prepared. A transmission image corresponding to an actual transmission amount of X-rays is picked up such that gray data corresponding to each of the regions a, b, c, d, e and f is recorded in the design data. When testing another electronic substrate, gray data detected at the regions a, b, c, d, e and f is compared with the recorded gray data, thus calculating transmission amounts of the X-rays at the regions a, b c, d, e and f. In this way, it is possible to easily test whether a defect is present in any of the interior (resist) of the substrate, the copper (Cu) films, the insulation films and the electrode layer formed below the insulation films. In other words, it is possible to perform a Die-database test using X-rays. Thus, the X-ray nondestructive testing device 10 can be applied not only in testing a pre-shipment product, but also in testing after the completion of a set of processes.

Measurement Process According to Sixth Embodiment

Figure 12:
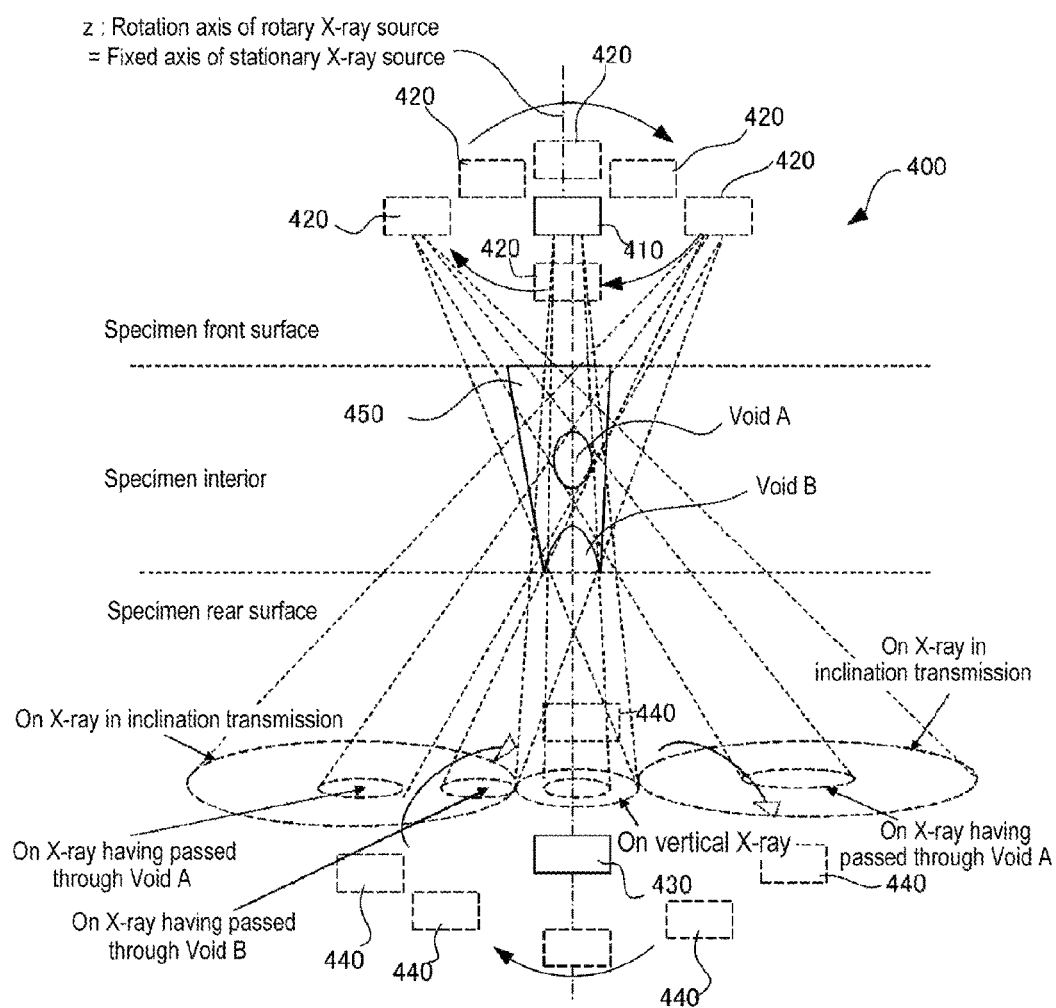
FIG. 12 is a view showing a process of measuring a thickness of each void formed in an article in a sixth embodiment of the present disclosure.
Figure 13:
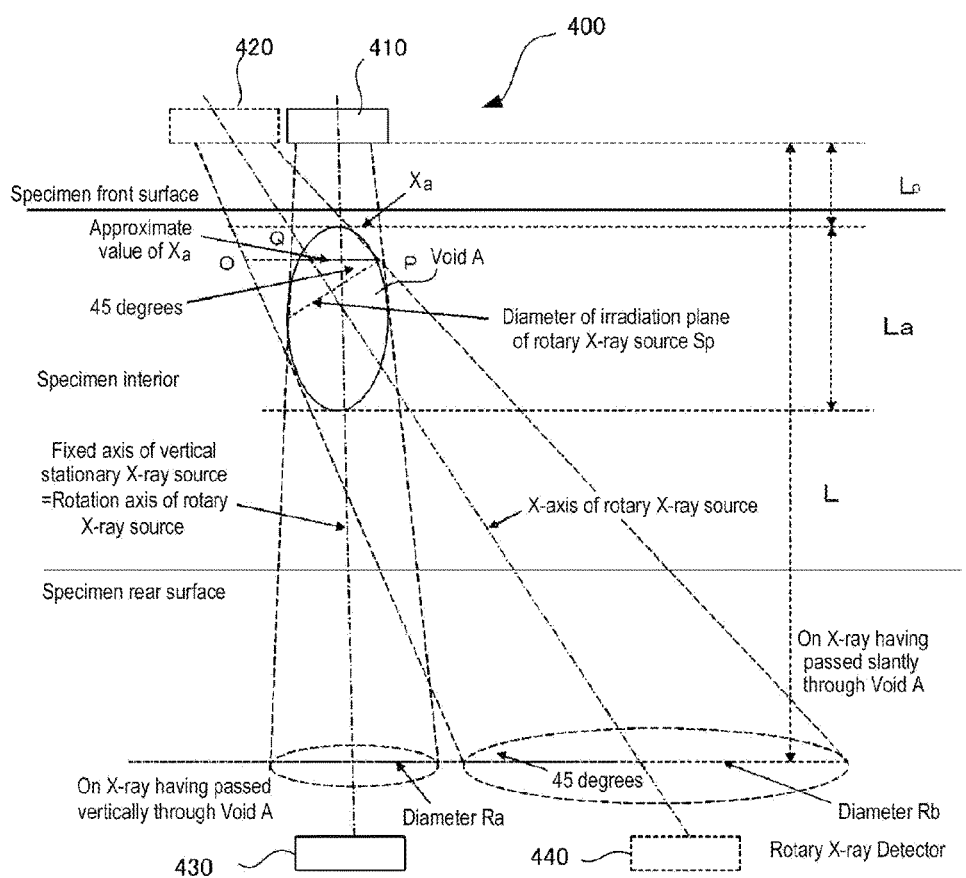
FIG. 13 is a view showing a process of measuring a shape of each void formed in the article in the sixth embodiment of the present disclosure.

Now, a sixth embodiment of the present disclosure in which a thickness or shape of a void (cavity) formed in a specimen is measured will be described. FIGS. 12 and 13 are views showing a process of measuring voids formed in a specimen using X-rays. In this embodiment, as shown in FIG. 12, an X-ray nondestructive testing device 400 includes a stationary X-ray source 410 and a rotary X-ray source 420 as X-ray sources, and a stationary detector 430 and a rotary detector 440 as detectors.

The stationary X-ray source 410 is disposed at the central portion of a specimen 450. The rotary X-ray source 420 is mounted on a rail or a U-shaped arm (not shown) and is disposed to rotate around the specimen 450. In addition, the stationary detector 430 is disposed to face the stationary X-ray source 410. The rotary detector 440 is fixed to a rail or a U-shaped arm (not shown) and is disposed at a location adapted to detect X-rays irradiated from the rotary X-ray source 420. The rotary X-ray source 420 rotates around a Z-axis in FIG. 12. The Z-axis also corresponds to a fixed axis in which the stationary X-ray source 410 is fixed. The X-ray nondestructive testing device 400 measures the thicknesses or the shapes of voids based on X-ray detection results obtained at the stationary detector 430 and the rotary detector 440.

In a case where a single void (see FIG. 13: void A) is formed in the specimen 450, the stationary X-ray source 410 and the rotary X-ray source 420 irradiate the X-rays along paths traveling through the void A and paths bypassing the void A. The stationary detector 430 and the rotary detector 440 detect amounts of the X-rays transmitted along the respective paths, thus calculating a thickness of the void A in a depth direction of the specimen 450 using the same calculation as in the above embodiments.

Further, the shape of the void A can be measured using a planar distribution of the transmission amounts of the X-rays passed through the specimen 450. A case where two voids, i.e., the void A and the void B, are formed to be distributed in the specimen 450 in a vertical direction as shown in FIG. 12 will be described. In this case, the X-rays are irradiated toward the specimen 450 in the vertical direction. Transmission amounts of the X-rays passed through the void A and the void B are measured. Subsequently, the rotary X-ray source 420 is rotated to be inclined at 45 degrees with respect to the vertical direction and irradiates the X-rays toward the specimen 450 at the inclined state. The rotary detector 440 is disposed in a point symmetrical relationship with the rotary X-ray source 420 with the specimen 450 interposed between the rotary X-ray source 420 and the rotary detector 440. In this way, the X-rays are irradiated toward the specimen 450 in directions corresponding to at least 6 locations.

The rotary X-ray source 420 irradiates the X-rays toward the void A of the specimen 450 such that the planar distribution of the transmission amounts of the X-rays passed through the void A is obtained. Likewise, the rotary X-ray source 420 is rotated to be disposed at another inclination direction. Thus, it is possible to obtain a transmission image of the rotary X-rays 420 passed through the specimen 450 in all the directions corresponding to the at least 6 locations.

The transmission image generally has an elliptical shape. Thus, it is possible to obtain factors of a to f by substituting coordinates of a periphery portion of the image in the following formula: $ax^2+by^2+cxy+dx+ey+f=0$ (a, b≠0), disposing the rotary X-ray source 420 at the at least 6 locations, and detecting transmission amounts of the X-rays passed through the specimen 450 at the at least 6 locations.

Using such an elliptical formula, a shape of a plane through which the X-rays are transmitted can be obtained from the inclination direction in which the X-rays are irradiated, e.g., at an angle of 45 degrees. When the X-rays are irradiated in the inclination direction at the angle of, e.g., 45 degrees, the following relationship can be established:

Diameter of the $X$-ray transmission plane=Image of elliptical shape/cos 45 degrees=$\sqrt{2}$×Image of elliptical shape Thus, by multiplying the elliptical shape with $\sqrt{2}$, the shape and coordinates of the X-ray transmission plane can be derived.

Based on the shape, a center coordinate and contour coordinates of the X-ray transmission plane, it is possible to obtain a shape, a center coordinate and contour coordinates of a transmission plane obtained by slicing the void A in rounds, thus obtaining a shape and contour coordinates of the void A in a horizontal direction. Further, it is possible to obtain a size of the void A in the horizontal direction.

Further, while in the above embodiment, the X-rays have been described to be transmitted through the void A in the direction inclined by the angle of 45 degrees, the X-rays may be transmitted through the void A in different inclination directions. Thus, as described above, it is possible to obtain a shape, a center coordinate and contour coordinates of a transmission plane obtained by slicing the void A in rounds at different points, thereby calculating a thickness of the void A in the depth direction of the specimen.

Further, based on the calculated thickness of the void A in the depth direction of the specimen 450 and the transmission amount of the X-rays passed through the void A, a thickness of the void B can be obtained using transmission amounts of the X-rays passed through both the void A and the void B.

As in the above embodiment, obtaining a size of the void B in the horizontal direction requires irradiating X-rays toward the void B of the specimen 450 using the rotary X-ray source 420 and detecting a transmission amount and a transmission image of the X-rays passed through the void B. Likewise, the rotary X-ray source 420 is rotated to be inclined in another inclination direction such that the X-rays are transmitted through the specimen 450 in inclination directions corresponding to the at least 6 locations at the angle of 45 degrees. Transmission amounts and transmission images of the X-rays passed through the specimen 450 are detected so that the size of the void B in the horizontal direction is obtained by the similar calculation to the above.

As described above, an X-ray nondestructive testing device according to the present disclosure can measure a thickness of a specified target object or a distance from a front surface of an article to the specified target object in a nondestructive manner, even for an electronic substrate or a wafer with various objects formed therein. That is to say, in a case where locations at which transmission amounts of X-rays are detected are specified based on a design information of a substrate stored in a memory, a set of paired different locations is specified in the substrate having a multilayered structure such that a difference between the transmission amounts of the X-rays at the paired locations is defined as a measurement target object. The transmission amounts of the X-rays passed through the paired locations are detected and compared with each other, thus easily measuring a thickness of the measurement target object within the multilayered structure through the use of a testing device employing a simple testing method at low cost, even for the multilayered structure in which a plurality of measurement target objects is incorporated in the substrate in stacked layers.

What is claimed is:

1. An X-ray nondestructive testing device which irradiates X-rays to an article, measures transmission amounts of the X-rays passed through the article and obtains a thickness of a measurement target object based on the transmission amounts, the article being fabricated based on a pre-stored design information and including a substrate having a predetermined X-ray absorption coefficient and the measurement target object disposed within the substrate and having another X-ray absorption coefficient differing from that of the substrate, the device comprising:
   an X-ray source configured to irradiate the X-rays to the article;
   a detector configured to detect the transmission amounts of the X-rays passed through the article at at least paired different locations specified in the article;
   a detection position specifying designator configured to specify the paired different locations as a set of paired locations based on the pre-stored design information such that a difference between transmission paths of the X-ray at the paired locations specified in the article is defined as the measurement target object;
   a driving mechanism configured to move the detector to the set of paired locations specified by the detection position specifying designator; and
   an operation calculator configured to calculate the thickness of the measurement target object based on the transmission amounts of the X-rays detected by the detector.

2. The X-ray nondestructive testing device of claim 1, wherein the measurement target object is formed in a single layer or in plural layers within the substrate.

3. The X-ray nondestructive testing device of claim 1, wherein the detection position specifying designator specifies the set of paired locations including a first location selected from one region in which the measurement target object is present, and a second location selected from another in which the measurement target object is not present, the second location being spaced apart from the one region in which the measurement target object is present by a minimum distance.

4. The X-ray nondestructive testing device of claim 1, wherein the detection position specifying designator specifies the set of paired location including a first location selected from one region in which the measurement target object is present and a second location selected from another region adjacent to the one region in which the measurement target object is present.

5. The X-ray nondestructive testing device of claim 1, wherein the detection position specifying designator specifies the set of paired location including a first location selected from one region in which the measurement target object is present, and a second location selected from another region in which the measurement target object is not present and adjacent to a border line between the one region and the another region.

6. The X-ray nondestructive testing device of claim 1, wherein the substrate of the article is provided with a plurality of measurement target objects,
   the detection position specifying designator specifies a first set of paired locations in the article such that a difference between transmission paths of the X-ray at the first set of paired locations is defined as a first measurement target object, the first set of paired locations including a first location selected from one region in which the measurement target object is not present and a second location selected from another region in which the measurement target object is present, and
   the operation calculator calculates a thickness of the first measurement target object at the second location based on transmission amounts of the X-rays which are measured at the first location and the second location of the first set of paired locations, and
   wherein the detection position specifying designator specifies a second set of paired locations in the article such that a difference between transmission paths of the X-ray at the first location and a third location is defined as a second measurement target object different from the first measurement target object, the second set of paired locations including the first location and the third location different from the first and second locations, and
   the operation means calculates a thickness of the second measurement target object at the third location based on transmission amounts of the X-rays which are measured at the first location and the third location of the second set of paired locations.

7. The X-ray nondestructive testing device of claim 1, wherein the substrate of the article is provided with a plurality of measurement target objects,
   the detection position specifying designator specifies a first set of paired locations in the article such that a difference between transmission paths of the X-ray at the first set of paired locations is defined as a first measurement target object, the first set of paired locations including a first location selected from one region in which the measurement target object is not present and a second location selected from another region in which the measurement target object is present, and
   the operation calculator calculates a thickness of the first measurement target object at the second location based on transmission amounts of the X-rays which are measured at the first and the second locations of the first set of paired locations, and
   wherein the detection position specifying designator specifies a second set of paired locations in the article such that a difference between transmission paths of the X-ray at the second location and a third location is defined as a second measurement target object different from the first measurement target object, the second set of paired locations including the second location and the third location different from the first and second locations, and the operation calculator calculates a thickness of the second measurement target object at the third location based on transmission amounts of the X-rays which are measured at the second location and the third location of the second set of paired locations.

8. The X-ray nondestructive testing device of claim 6, wherein the detection position specifying means specifies a third set of paired locations in the article such that a difference between transmission paths of the X-ray at the third location and a fourth location is defined as a third measurement target object different from the first and second measurement target objects, the third set of paired locations including the third location and the fourth location different from the first to third locations, and the operation calculator calculates a thickness of the third measurement target object at the fourth location based on transmission amounts of the X-rays which are measured at the second location and the third location of the third set of paired locations.

9. The X-ray nondestructive testing device of claim 6, wherein the detection position specifying designator specifies a third set of paired locations in the article such that a difference between transmission paths of the X-ray at the second or third location and a fourth location is defined as a third measurement target object different from the first and second measurement target objects, the third set of paired locations including the second or third location and the fourth location different from the first to third locations, and the operation calculator calculates a thickness of the third measurement target object at the fourth location based on transmission amounts of the X-rays which are measured at the second or third location and the fourth location of the third set of paired locations.

10. An X-ray nondestructive testing device which irradiates X-rays to an article, measures transmission amounts of the X-rays passed through the article and obtains a cross sectional shape of a region in which a measurement target object is present, based on the transmission amounts, the article being fabricated based on a pre-stored design information and including a substrate having a predetermined X-ray absorption coefficient and the measurement target object disposed within the substrate and having another X-ray absorption coefficient differing from that of the substrate, the device comprising:

an X-ray source configured to irradiate the X-rays to the article;

a detector configured to detect the transmission amounts of the X-rays passed through the article at at least paired different locations specified in the article;

a detection position specifying designator configured to specify the paired different locations as a set of paired locations based on the pre-stored design information of the substrate such that a difference between transmission paths of the X-rays at the paired locations is defined as the measurement target object, wherein when a border line is defined between one region in which the measurement target object specified by the design information is present and another region in which no measurement target object is present, the set of paired locations includes: a first set of paired locations selected from the one region; a second set of paired locations including one location selected from the one region and one location selected from the border line; a third set of paired locations including one location selected from the one region and one location selected from the another region; and a fourth set of paired locations including one location selected from the one region and one location selected from the another region, which is spaced apart from the border line by a predetermined distance in a direction traversing the border line, a driver configured to move the detector means to the set of paired locations specified by the detection position specifying designator; and an operation calculator configured to calculate the cross sectional shape of the one region in which the measurement target object is present, based on the transmission amounts of the X-rays detected by the detection means.

11. The X-ray nondestructive testing device of claim 1, wherein the detection position specifying designator specifies two sets of paired locations selected from a region in which a certain measurement target object is disposed, the two sets of paired locations being spaced apart from each other in the article.

12. The X-ray nondestructive testing device of claim 1, wherein the detection position specifying designator selects the set of paired locations from a region in which the number of layers constituting the measurement target object is small.

13. The X-ray nondestructive testing device of claim 1, wherein the detection position specifying designator selects the set of paired locations from a central portion of a stage on which the article is mounted.

14. The X-ray nondestructive testing device of claim 1, wherein the design information includes a design diagram, a circuit diagram, or a circuit cross-sectional diagram.

* * * * *